United States Patent
Boussignac

(10) Patent No.: US 6,458,097 B1
(45) Date of Patent: *Oct. 1, 2002

(54) CATHETER FOR CORPOREAL DUCT

(76) Inventor: Georges Boussignac, 1 Avenue de Provence, Antony (FR), 92160

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/380,822
(22) PCT Filed: Jan. 21, 1999
(86) PCT No.: PCT/FR99/00117
§ 371 (c)(1),
(2), (4) Date: Sep. 10, 1999
(87) PCT Pub. No.: WO99/37355
PCT Pub. Date: Jul. 29, 1999

(30) Foreign Application Priority Data

Jan. 22, 1998 (FR) .............................................. 98 00652

(51) Int. Cl.[7] .............................................. A61M 29/00
(52) U.S. Cl. .............................. 604/96.01; 604/103.06; 604/103.08; 606/192
(58) Field of Search .............................. 604/48, 93.01, 604/95.04, 96.01, 103.05, 103.06, 103.08, 103.14, 158, 163, 164.01, 164.1, 216, 264, 523, 525; 251/4–5, 117–118; 138/118–119, 121, 122, 123

(56) References Cited

U.S. PATENT DOCUMENTS

| | | | |
|---|---|---|---|
| 4,593,690 A | | 6/1986 | Sheridan et al. |
| 4,966,202 A | * | 10/1990 | Bryan et al. |
| 5,415,634 A | | 5/1995 | Glynn et al. |
| 5,466,222 A | | 11/1995 | Ressemann et al. |
| 6,123,712 A | * | 9/2000 | Di Caprio et al. |
| 6,179,827 B1 | * | 1/2001 | Davis et al. |

* cited by examiner

Primary Examiner—Brian L. Casler
Assistant Examiner—LoAn H. Thanh
(74) Attorney, Agent, or Firm—Fisher, Christen & Sabol

(57) ABSTRACT

The invention concerns a catheter (1) designed to be inserted in a corporeal duct and comprising a flexible elongated body, rigid in traction, including a sealed tubular sheath (3) for transmitting a fluid under pressure and capable of being subjected to radial collapse. Said catheter is characterized in that said sheath (3) is made at least partially of a flexible material and has a thin wall (4) with uneven surface, such that, when said sheath (3) is subjected to such a radial collapse, the irregularities at the surface thereof maintain a fluid communication (7) between said sheath (3) ends.

5 Claims, 1 Drawing Sheet

CATHETER FOR CORPOREAL DUCT

This is a 371 National Stage Application of PCT/FR99/00117, filed on Jan. 21, 1999, which has priority benefit of French application 9800652, filed on Jan. 22, 1998.

The present invention relates to a catheter intended to be introduced into a body channel and including a flexible elongate body, rigid in traction, which comprises a leaktight tubular sheath for transmitting a pressurized fluid.

For treating stenoses of the coronary arteries, esophagus, urethra, etc., for example, dilatation catheters are already known which include an inflatable balloon which is arranged at the distal end of the said catheters and which, from the proximal end of the catheters, can be supplied with an inflation fluid via a leaktight tubular sheath for fluid transmission incorporated in the catheters. Thus, when the catheter has been introduced into the body channel as far as the area of the stenosis, the balloon is inflated by supplying it with an inflation fluid by way of the sheath, and the walls of the stenosis are spread apart by the balloon so as to re-establish a satisfactory passage through the said body channel.

Frequently, the leaktight sheath for transmitting pressurized fluid is arranged, at least at the distal end of the catheter, peripheral to the latter and forms the outer surface of it. Moreover, to avoid any risk of the gas communication through the sheath being interrupted by the radial collapse thereof, the sheath is made in the form of a flexible tube, which is radially rigid. Consequently, it is not possible to give the sheath as small an external diameter as would be needed to enter small body channels or pass through stenoses blocking almost the whole of such a body channel. This therefore results either in the complete impossibility of using such dilatation catheters, so that there is no solution other than to perform major surgery in order to remove the stenosis, or in considerable friction against the walls of the body channels (or against the walls of any tubular guide for positioning the catheter) making it difficult to advance the catheters inside the body.

When the radially rigid, leaktight sheath for transmitting fluid is incorporated inside the catheter, the same disadvantages result, because its necessarily large diameter imposes a similarly large diameter on the said catheter.

The object of the present invention is to remedy these disadvantages.

To this end, according to the invention, the catheter of the type mentioned above is distinguished by the fact that the leaktight tubular sheath for transmitting a pressurized fluid is made at least partly, particularly at the distal end, of a flexible material and has a thin wall with an irregular surface so that when the sheath undergoes radial collapse, the surface irregularities thereof leave a fluid communication remaining between the ends of the sheath.

A flexible sheath is thus obtained which, in the tensioned or inflated state (when pressurized fluid is passing through it), can present a very small diameter and which, in the relaxed or deflated state (when pressurized fluid is not passing through it), has an even smaller diameter, while nevertheless providing fluid communication along its length. When the flexible sheath itself envelops one or more elongate elements of the catheter, for example tubular elements, it will be readily appreciated that its radial size is scarcely any greater than that of the elements, even in the inflated state.

Moreover, it will be noted that because of the roughnesses of the surface of the sheath, the contact surface between the sheath and the body channel (or the tubular guide for positioning the catheter) is greatly reduced, which makes it easier to advance the catheter in the said body channel.

The flexible material from which the sheath in accordance with the present invention is made may be synthetic and for example a polyethylene, a polyamide or a polyether terephthalate. The thickness of the wall of the sheath can be from a few microns to a few tens of microns.

The thin sheath with irregular surface can be obtained by means of a flexible thin-walled tube, made for example by extrusion of the materials, being shaped hot and under pressure on a mandrel whose surface has irregularities. Such a mandrel can consist of a helical spring or the like impressing a hollow helical ribbing in the wall of the said tube. It will be noted that such a helical rib, in addition to its anti-collapse effect mentioned above, also makes it possible to increase the radial resistance to crushing of the said flexible sheath.

It will be noted that document U.S. Pat. No. 5,466,222 describes a catheter provided with internal and external bellows intended to be compressed longitudinally.

From the figures on the attached drawing, it will be clearly understood how the invention can be realized. In these figures, identical reference numbers designate similar elements.

Figure 1:
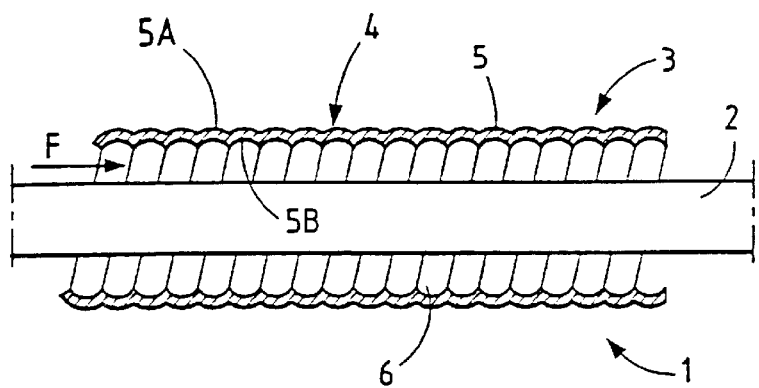
FIG. 1 is a diagrammatic axial section of a distal part of a catheter including a sheath in accordance with the present invention, the sheath being in the inflated state.
Figure 2:
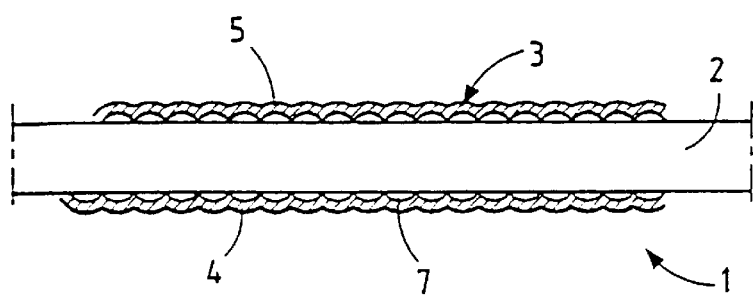
FIG. 2 is a view similar to FIG. 1, with the sheath in the deflated state.

The distal part 1 of the flexible catheter shown diagrammatically in FIGS. 1 and 2 include one or more elongate internal elements 2 which are surrounded by a flexible and leaktight sheath 3. At least some of the elements 2 are rigid in traction.

The flexible and leaktight sheath 3 is made of a film of polyethylene, polyamide or polyether terephthalate, with a wall thickness of between a few microns and a few tens of microns.

A helical ribbing with contiguous turns 5 is impressed in the thin wall 4 of the sheath 3. The convexity of each turn 5 is for example directed toward the outside of the catheter, while the concavity of the turns is then situated facing the internal elements 2.

Thus, when a pressurized fluid is introduced (arrows F in FIG. 1) between the said internal elements 2 and the said flexible sheath 3, the latter is tensioned and an annular space 6 appears between the said internal elements 2 and the said flexible sheath 3. By contrast, when no pressurized fluid is introduced between the said internal elements 2 and the said flexible sheath 3, the latter is relaxed and bears at least partially on the said internal elements 2, while nevertheless forming a helical space 7 with these, along its entire length, because of the existence of the helical ribbing.

Figure 3:
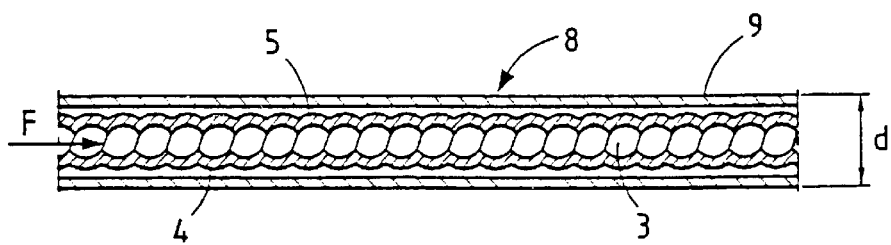
FIGS. 3 and 4 are diagrammatic axial sections of a distal part of a variation of the catheter including a sheath in accordance the present invention, in the inflated state and the deflated state, respectively.
Figure 4:
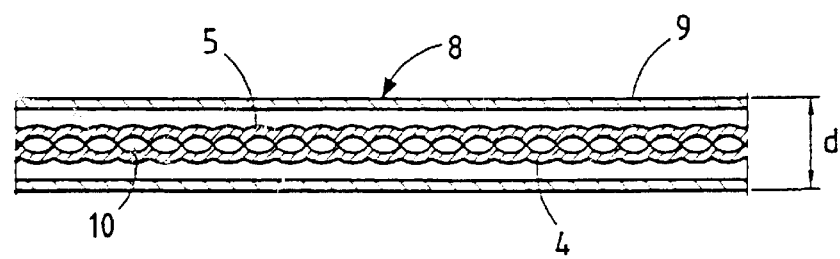

In the catheter 8 in FIGS. 3 and 4, the sheath 3 in accordance with the present invention is enclosed in an outer tube 9. Even in the inflated state (FIG. 3), the flexible sheath 3 occupies a small radial space, so that the diameter d of the said catheter 8 can be reduced. In the deflated state (FIG. 4), the radial space occupied by the flexible sheath 3 is reduced even more, but a helical passage 10 is formed along its entire length because of the existence of the ribbing 5.

Of course, although the present invention was introduced at the outset with a presentation of the disadvantages of dilatation catheters, the present invention is not limited to this particular type of catheter and it can be implemented whenever a catheter, which is flexible and rigid in traction, includes a leaktight tubular sheath for transmitting a pressurized fluid. Moreover, although FIGS. 1 to 4 show the sheath 3 as shaped on the outer surface of a helical spring, it goes without saying that the sheath could have been shaped on the inner surface of such a spring.

What is claimed is:

1. Catheter intended to be introduced into a body channel and comprising: at least one flexible elongate internal element, rigid in traction, and a leaktight tubular sheath surrounding said internal element with an annular space formed between said internal element and said sheath and used for transmitting a pressurized fluid, said sheath being made of a flexible material, having a thin wall and being capable of undergoing radial collapse when no pressurized fluid is introduced into said annular space wherein said thin wall has a surface with irregularities so that when said sheath undergoes such a radial collapse and bears on said internal element, said irregularities maintain a space between said internal element and said sheath for fluid communication between and beyond the ends of said sheath, there being fluid flow capability at all times completely through said and beyond annular space or said space.

2. Catheter according to claim 1, characterized in that the flexible material of which the said sheath is made is a synthetic material such as a polyethylene, a polyamide or a polyether terephthalate.

3. Catheter according to claim 1, characterized in that the said thin sheath with an irregular surface is obtained by means of a flexible thin-walled tube being shaped hot and under pressure on a mandrel whose outer surface has irregularities.

4. Catheter according to claim 1, characterized in that a helical ribbing is impressed in the wall of the said thin sheath.

5. Catheter according to claim 1, characterized in that the said flexible sheath forms, at least in part, the outer surface of the said catheter.

* * * * *